(12) United States Patent
Bialek et al.

(10) Patent No.: US 6,498,197 B1
(45) Date of Patent: Dec. 24, 2002

(54) TEMPERATURE INSENSITIVE ONE-PHASE MICROEMULSIONS

(75) Inventors: Aneta Ilona Bialek, Bay City, MI (US); Randal Myron Hill, Midland, MI (US); Donald Anthony Kadlec, Midland, MI (US); Heidi Marie Van Dort, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/912,951

(22) Filed: Jul. 25, 2001

(51) Int. Cl.$^7$ .................................................. B01F 3/08
(52) U.S. Cl. .................. 516/55; 556/444; 556/445; 524/588; 524/837
(58) Field of Search ................ 556/444, 445; 524/588, 837; 516/55

(56) References Cited

U.S. PATENT DOCUMENTS

| | | | |
|---|---|---|---|
| 4,122,029 A | 10/1978 | Gee et al. | 252/309 |
| 4,265,878 A | 5/1981 | Keil | 424/68 |
| 4,268,499 A | 5/1981 | Keil | 424/68 |
| 4,620,878 A | 11/1986 | Gee | 106/287.15 |
| 5,705,562 A | 1/1998 | Hill | 524/731 |
| 5,707,613 A | 1/1998 | Hill | 424/78.03 |
| 5,972,356 A | * 10/1999 | Peffly et al. | |
| 6,013,683 A | 1/2000 | Hill et al. | 516/67 |

OTHER PUBLICATIONS

Journal of Colloid and Interface Science, "Water Solubilization in Nonionic Microemulsions Stabilized by Grafted Siliconic Emulsifiers", vol. 233, pp. 286–294, 2001.
Progress in Colloid and Polymer Science, "Phase Behavior of Polyoxyethylene Modified Silicone with Water", vol. 110, pp. 225–229, 1998.

* cited by examiner

*Primary Examiner*—Robert Dawson
*Assistant Examiner*—Kuo-Liang Peng
(74) *Attorney, Agent, or Firm*—Timothy J. Troy

(57) ABSTRACT

This invention relates to an optically clear one-phase microemulsion which is transparent at a temperature range of from 0–70° C. comprising (i) at least one non-aqueous polar solvent, (ii) at least one non-polar solvent immiscible with (i), and (iii) at least one oxyalkylene-containing polydiorganosiloxane. The microemulsions of this invention are useful as delivery vehicles for personal care active ingredients such as antiperspirant salts, sunscreens, alpha-hydroxy fatty acids, and Vitamin E.

31 Claims, No Drawings

TEMPERATURE INSENSITIVE ONE-PHASE MICROEMULSIONS

BACKGROUND OF THE INVENTION

This invention relates to an optically clear one-phase microemulsion which is transparent throughout a temperature range of from 0 to 70° C. comprising (i) at least one non-aqueous polar solvent, (ii) at least one non-polar solvent immiscible with (i), and (iii) at least one oxyalkylene-containing polydiorganosiloxane. The microemulsions of this invention are useful in personal care products.

Transparent mixtures of low molecular weight silicone oils using polymeric silicone surfactants have been described. For example, Gee in U.S. Pat. No. 4,620,878 discloses a method of preparing fine polyorganosiloxane emulsions with an average particle size of less than 0.3 micron and polyorganosiloxane microemulsions with an average particle size of less than 0.14 micron by preparing a translucent oil concentrate by mixing a polyorganosiloxane which contains polar groups, a surfactant which is insoluble in the polyorganosiloxane, and sufficient water to obtain a translucent mixture, the translucent oil concentrate is then rapidly dispersed in water to form the desired fine emulsion or microemulsion. Gee further discloses that if the translucent oil concentrate is not transparent a fine emulsion with an average particle size of less than 0.3 micron is obtained; whereas, if the oil concentrate is transparent, a microemulsion with an average particle size of less than 0.14 micron is obtained.

Gee et al. in U.S. Pat. No. 4,122,029 discloses stable emulsions of a polar liquid in a non-polar base liquid are prepared with the cooperating action of a mixture of a water-in-oil surfactant having an HLB value of from 2 to 10 and certain polydiorganosiloxane-polyoxyalkylene copolymers. Gee et al. Gee further discloses an antiperspirant composition comprising an aqueous solution of aluminum chlorohydrate as the polar liquid dispersed in cyclopolydimethylsiloxanes as the non-polar base liquid, using a mixture of nonylphenoxy polyethoxyethanol and a copolymer of a trimethylsiloxy-endblocked polydimethylsiloxane containing a minor amount of methylhydrogensiloxane units and an allyloxy-endblocked polyoxyethylenepolyoxypropylene copolymer.

Keil in U.S. Pat. No. 4,265,878 discloses antiperspirant stick compositions which comprise an aqueous solution of an astringent dispersed in a solid matrix comprising a volatile, water-insoluble liquid, a polydiorganosiloxane-polyoxyalkylene copolymer, a solid alkanoic acid, a waxy ester, and optionally containing a solid alkanol. Keil discloses that a preferred embodiment comprises an aqueous solution of aluminum chlorohydrate dispersed in a solid matrix comprising cyclopolydimethylsiloxanes as the volatile liquid. Keil further discloses that these compositions are stable to separation in the molten state and provide non-leaking sticks of controllable softness when solidified by cooling.

Keil in U.S. Pat. No. 4,268,499 discloses antiperspirant emulsion compositions which comprise an aqueous solution of an astringent agent; a volatile, water-insoluble liquid, a polydiorganosiloxane-polyoxyalkylene copolymer, an oil-in-water type surfactant, and a water-in-oil type surfactant. Keil discloses that a preferred embodiment comprises an emulsion of aqueous aluminum chlorohydrate in cyclopolydimethylsiloxanes as the volatile fluid and that these compositions have improved efficacy as measured by their drying times.

Microemulsions of low molecular weight silicone oils with hydrocarbon surfactants have been disclosed. For example, Hill et al. in U.S. Pat. No. 6,013,683 discloses a clear single phase composition containing 40–95% by weight of a cyclic or short chain linear methyl siloxane and water, and 5–60% by weight of a cationic surfactant and a nonionic surfactant. Hill et al. discloses that the cyclic or short chain linear methyl siloxane in the single phase composition has an average structure or droplet diameter of less than about 50 nanometer. Hill et al. further discloses that the single phase composition spontaneously provides optically clear one phase silicone microemulsions when combined with only hand agitation and that the clear single phase compositions are useful in personal care and textile applications.

Microemulsions of low molecular weight silicone oils using trisiloxane surfactants have been disclosed. For example, Hill in U.S. Pat. Nos. 5,705,562 and 5,707,613 discloses a method of spontaneously forming a highly stable clear microemulsion by combining (i) water, (ii) a volatile cyclic methyl siloxane or volatile linear methyl siloxane, and (iii) a silicone polyether surfactant. Hill discloses that the amounts of each component are such that the composition is in the form of a microemulsion and that the volatile methyl siloxane is present in the microemulsion in the form of particles having an average diameter of less than about 100 nanometers. Hill discloses that the microemulsion is useful in personal care products.

Microemulsions containing octanol, decanol, or dodecanol as the oil phase and oligomeric, grafted nonionic amphiphiles based on ethoxylated polydimethylsiloxanes have been disclosed, for example in Garti et al., *Journal of Colloid and Interface Science*, Vol. 233, pp. 286–294 (2001). The surfactants of Garti et al. were two trisiloxanes and an oxyalkylene containing polydimethylsiloxane having the formula $Me_3SiO(Me_2SiO)_4(MeRSiO)_3SiMe_3$ where R is a group having the formula $—(CH_2)_3(OCH_2CH_2)_{10}OH$. Garti et al. disclose that significant amounts of water could be solubilized only for the trisiloxane surfactants.

Iwanaga et al. in *Progress in Colloid & Polymer Science*, Vol. 110, pp. 225–229 (1998), disclose isothermal phase diagrams for two oxyalkylene-containing polydiorganosiloxanes with water and a cyclosiloxane having the structure $—(MeSiO)_4—$ showing $L_\alpha$ and $H_2$ liquid crystal phases, and a narrow region of oil-rich microemulsion along the oil-surfactant axis.

SUMMARY OF THE INVENTION

This invention relates to an optically clear one-phase microemulsion which is transparent throughout temperature range of from 0 to 70° C. comprising (i) at least one non-aqueous polar solvent, (ii) at least one non-polar solvent immiscible with (i), and (iii) at least one oxyalkylene-containing polydiorganosiloxane. The microemulsions of this invention are useful as delivery vehicles for personal care actives such as antiperspirant salts, sunscreens, alpha-hydroxy fatty acids, and Vitamin E.

It is an object of this invention to prepare optically clear one-phase microemulsions which are transparent at a temperature of 0 to 70° C.

DETAILED DESCRIPTION OF THE INVENTION

This invention relates to an optically clear one-phase microemulsion which is transparent at a temperature of 0 to 70° C. comprising (i) at least one non-aqueous polar solvent, (ii) at least one non-polar solvent immiscible with (i), and
(iii) at least one oxyalkylene-containing polydiorganosiloxane having its formula selected from the group consisting of $R_3SiO(RR^1SiO)_ySiR_3$, $R_3SiO(R_2SiO)_x(RR^1SiO)_ySiR_3$, $R^1R_2SiO(RR^1SiO)_zSiR_2R^1$, $R^1R_2SiO(R_2SiO)_xSiR_2R^1$, $R^1R_2SiO(R_2SiO)_x(RR^1SiO)_zSiR_2R^1$, and a cyclosiloxane copolymer having the formula $—(Me_2SiO)_m(MeR^1SiO)_n—$ wherein R denotes an alkyl group containing from 1 to 6 carbon atoms, $R^1$ denotes a group having its formula selected from the group consisting of $—(CH_2)_a(OCH_2CH_2)_bOR^2$, $—(CH_2)_a(OCH_2CH(CH_3))_cOR^2$, $—(CH_2)_a(OCH_2CH(CH_2CH_3))_dOR^2$, $—(CH_2)_a(OCH_2CH_2)_b(OCH_2CH(CH_3))_cOR^2$, $—(CH_2)_a(OCH_2CH_2)_b(OCH_2CH(CH_2CH_3))_dOR^2$, and $—(CH_2)_a(OCH_2CH_2)_b(OCH_2CH(CH_3))_c(OCH_2CH(CH_2CH_3))_dOR^2$ wherein a has a value of 3 to 11, b has a value of 1 to 20, c has a value of 1 to 10, d has a value of 1 to 4, and $R^2$ is selected from the group consisting of hydrogen, an alkyl group, and an acyl group, x has a value of 1 to 400, y has a value of 1 to 40, z has a value of 1 to 40, m has a value of 1 to 6, n has a value of 1 to 6, and the value of m+n is from 3 to 6.

Microemulsion as defined herein denotes a one-phase transparent mixture of (i) two immiscible fluids, for example, a non-polar oil and a polar solvent, and (ii) at least one amphiphile (exemplified by surfactants). The particle size of the resulting droplets is small enough so the resulting mixture is clear or translucent. Because of their relative clarity microemulsions are distinguishable from standard opaque emulsions in that certain microemulsions can be used to prepare clear cosmetics. The clarity of these compositions is advantageous in cosmetic applications.

Microemulsions are typically more stable than standard emulsions, however, microemulsions containing polyoxyalkylene surfactants usually show a narrow temperature range of stability. The present invention however does not have this temperature sensitivity. Microemulsion droplet sizes are variously defined in the art with an upper limit on the droplet size typically being placed somewhere between 0.10 and 0.15 micron to distinguish microemulsions from opaque standard emulsions. In general, microemulsions can also be defined by their appearance: microemulsions are transparent or translucent, and do not display the opalescence of standard emulsions. While microemulsions with average droplet sizes between 0.10 and 0.15 micron display the properties of microemulsions, microemulsions with average droplet sizes less than 0.10 micron are especially preferred for their even greater clarity.

For the purposes of this invention, the term "optically clear" is used to define a composition that is "transparent" (i.e. transmitting light without distortion) which means that the size of the particles in the composition are reduced to a size where they are not observable with optical (visual) means. Transmitting light without distortion as used herein means being able to read 12-point text through a 1-centimeter thick sample of the microemulsion.

The non-aqueous polar solvent of Component (i) is exemplified by abietyl alcohol, n-acetyl dihydrosphingosine, alcohol denat, arachidyl glycol, batyl alcohol, benzyl alcohol, benzyl glycol, benzyl ursolate, bisabolol, bishydroxyethyl biscetyl malonamide, borneol, 2-bromo-2-nitropropane-1,3-diol, 1,4-butanediol, butoxydiglycol, butoxyethanol, butoxyisopropanol, n-butyl alcohol, t-butyl alcohol, 2-t-butylcyclohexyloxybutanol, butylene glycol, butyloctanol, C20–40 alcohols, C30–50 alcohols, C40–60 alcohols, C18–38 alkyl hydroxystearoyl stearate, camphylcyclohexanol, caproyl sphingosine, caprylyl glycol, CD alcohol 19, ceramide 1, ceramide 2, ceramide 3, ceramide 4, ceramide 5, ceramide 1 A, ceramide 6 II, cetylarachidol, cetyl glycol, cetyloxypropyl glyceryl methoxypropyl myristamide, C9–13 fluoroalcohol, C14–18 glycol, C15–18 glycol, C18–30 glycol, C20–30 glycol, chimyl alcohol, chlorobutanol, chlorphenesin, cholecalciferol, cholesterol, cinnamyl alcohol, citronellol, darutoside, decyltetradecanol, 7-dehydrocholesterol, diacetone alcohol, 2,4-diaminophenoxyethanol sulfate, dichlorobenzyl alcohol, diethylene glycol, dihydrocholesterol, dihydrolanosterol, dihydroxyacetone, dihydroxyethylamino hydroxypropyl oleate, 2,6-dimethyl-7-octen-2-ol, dimethyl octynediol, dimethyl phenylpropanol, dipropylene glycol, dithiothreitol, dodecylhexadecanol, dodecyltetradecanol, ergocalciferol, erythrulose, ethoxydiglycol, ethoxyethanol, ethyl ascorbyl ether, ethylhexylglycerin, ethylhexylglyceryl behenate, farnesol, galactonolactone, geraniol, glycyrrhetinic acid, glycyrrhizic acid, heptylundecanol, hexacosyl glycol, hexyldecanol, hexyldecyloctadecanol, hinokitiol, hydroabietyl alcohol, hydrogenated ethylbicycloheptane guaiacol, hydrolyzed glycyrrhizinate, hydroxycapric acid, hydroxycaproyl phytosphingosine, hydroxycaprylic acid, hydroxycapryloyl phytosphingosine, hydroxyethyl isobutyl piperidine carboxylate, hydroxyethyl palmityl oxyhydroxypropyl palmitamide, hydroxylated methyl soyate trimethylolpropane ether, hydroxylauric acid, hydroxylauroyl phytosphingosine, hydroxymethyl dioxoazabicyclooctane, hydroxypalmitoyl sphinganine, hydroxyproline, hydroxypropyl ethylenediamine carbomer, hydroxystearyl cetyl ether, isoamyl alcohol, isobutoxypropanol, isobutyl methyl tetrahydropyranol, isocetyl alcohol, isopentyldiol, isopropyl alcohol, isopulegol, isostearyl alcohol, lactoyl phytosphingosine, lanolin alcohol, lauryl alcohol diphosphonic acid, lauryl glycol, linalool, menthanediol, p-menthan-7-ol, menthol, menthone glycerin acetal, menthoxypropanediol, 3-methoxybutanol, methoxyethanol, methoxyisopropanol, methoxymethylbutanol, methoxytrimethylphenyl dihydroxyphenyl propanol, methyl alcohol, 3-methylamino-4-nitrophenoxyethanol, methyl glycyrrhizate, 2-methyl-4-hydroxypyrrolidine, methyl lactate, methyl lactic acid, methyl phenylbutanol, methylsilanol glycyrrhizinate, methylsilanol hydroxyproline, myrcenol, myricyl alcohol, neopentyl glycol, nicotinyl alcohol, nicotinyl tartrate, ninhydrin, 3-nitro-4-aminophenoxyethanol, octacosanyl glycol, octyldecanol, octyldodecanol, 2-oleamido-1,3-octadecanediol, palmitamidohexadecanediol, panthenol, panthenyl ethyl ether, panthenyl hydroxypropyl steardimonium chloride, pantolactone, pentadecyl alcohol, pentylene glycol, phenethyl alcohol, phenoxyethanol, phenoxyisopropanol, phenylisohexanol, phenylpropanol, phytosphingosine, phytosphingosine HCl, polyvinyl alcohol, potassium lauryl hydroxypropyl sulfonate, propanediol, propyl alcohol, propylene glycol, pyridoxine glycyrrhetinate, retinol, ribonolactone, salicyloyl phytosphingosine, SD Alcohol 1, SD Alcohol 3-A, SD Alcohol 3-B, SD Alcohol 3-C, SD Alcohol 23-A, SD Alcohol 23-F, SD Alcohol 23-H, SD Alcohol 27-B, SD Alcohol 30, SD Alcohol 31-A, SD Alcohol 36, SD Alcohol 37, SD Alcohol 38-B, SD Alcohol 38-C, SD Alcohol 38-D, SD Alcohol 38-F, SD Alcohol 39, SD Alcohol 39-A, SD Alcohol 39-B, SD Alcohol 39-C, SD Alcohol 39D, SD Alcohol 40, SD Alcohol 40-A, SD Alcohol 40-B, SD Alcohol 40-C, SD Alcohol 46, sphinganine, n-stearoyl-dihydrosphingosine, stearoyl phytosphingosine, stearyl glycol, terpineol, tetraacetylphytosphingosine, tetradecyleicosanol, tetradecyloctadecanol, tetrahydrofurfuryl alcohol, tetramethyl cyclopentene butenol, tetramethyl decynediol, tridecyl alcohol, triethylene glycol, trimethylhexanol, trimethyl hydroxymethyl cyclohexanol, trimethyl hydroxypentyl isobutyrate, trimethyl pentanol hydroxyethyl ether, troxerutin, undeceth-3, undecyl alcohol, undecylenyl alcohol, undecylpentadecanol, p-anisic acid, arachidyl glucoside, batyl alcohol, batyl isostearate, batyl stearate, benzyl glycol, benzylhemiformal, 1,3-bis-(2,4-diaminophenoxy)propane, 5-bromo-5-nitro-1,3-dioxane, butoxydiglycol, butoxyethanol, butoxyethyl acetate, butoxyethyl nicotinate, butoxyethyl stearate, butoxyisopropanol, 2-t-butylcyclohexyloxybutanol, butyl glucoside, butylglucoside caprate, butyl methoxydibenzoylmethane, C12–20 alkyl glucoside, caprylyl/capryl glucoside, caprylyl glucoside, caprylyl glyceryl ether, capsaicin, carboxymethyl chitin, carboxymethyl chitosan succinamide, carboxymethyl dextran, cetearyl glucoside, cetearyl wheat straw glycosides, cetyl dimethylbutyl ether, cetyl glyceryl ether, cetyl glyceryl ether-glycerin copolymer, cetyloxypropyl glyceryl methoxypropyl myristamide, cetyl-PG hydroxyethyl decanamide, cetyl-PG hydroxyethyl palmitamide, chimyl alcohol, chimyl isostearate, chimyl stearate, chlorphenesin, C12–14 hydroxyalkyl maltitol ether, cinoxate, cocamidopropyl lauryl ether, coceth-4 glucoside, coco-glucoside, corn starch modified, curcumin, DEA-methoxycinnamate, decyl glucoside, deltamethrin, demethoxycurcumin, diallyloxyneohexyl zirconium tridecanoate, 2,4-diaminophenoxyethanol sulfate, dibenzylidene, dicaprylyl ether, dicetyl ether, dichlorophenyl imidazoldioxolan, diethylene glycol, dimethicone copolyol butyl ether, dimethicone copolyol ethyl ether, dimethicone copolyol methyl ether, dimethoxy di-p-cresol, dimethoxydiglycol, dimethyl ether, dimethyl hexahydronaphthyl dihydroxymethyl acetal, dimethyl isosorbide, dimethylmethoxy chromanol, dioleyl tocopheryl methylsilanol, diosmine, dioxolane, dipropylene glycol, dipropylene glycol dimethyl ether, disodium cetyl phenyl ether disulfonate, disodium decyl phenyl ether disulfonate, disodium lauryl phenyl ether disulfonate, distarch glyceryl ether, distearyl ether, ethoxydiglycol, ethoxydiglycol acetate, ethoxydiglycol behenate, ethoxydiglycol isostearate, ethoxydiglycol oleate, ethoxyethanol, ethoxyethanol acetate, ethoxyheptyl bicyclooctanone, ethyl ascorbyl ether, 7-ethylbicyclooxazolidine, ethylcellulose, ethyl ether, ethyl glucoside, ethylhexyl ferulate, ethylhexylglycerin, ethylhexylglyceryl behenate, ethylhexylglyceryl palmitate, ethylhexyloxyglyceryl palmitate, ethyl methoxycinnamate, ethyl methylphenylglycidate, ethyl phenethyl acetal, eucalyptol, eugenol, eugenyl acetate, eugenyl glucoside, ferulic acid, glyceryl dimaltodextrin, glyceryl ethylhexanoate dimethoxycinnamate, glycofurol, hesperetin laurate, hexamethylindanopyran, hexamidine, hexamidine diparaben, hexamidine paraben, hydrogenated ethylbicycloheptane guaiacol, p-hydroxyanisole, hydroxydecyl maltitol, hydroxydichlorodiphenyl ether, hydroxyethyl glyceryl oleate/stearate, hydroxyethyl isostearyloxy isopropanolamine, hydroxyethyl palmityl oxyhydroxypropyl palmitamide, hydroxyethyl sorbitol, hydroxylated methyl soyate trimethylolpropane ether, hydroxymethoxybenzyl pelargonamide, hydroxypropyl arginine lauryl/myristyl Ether HCl, hydroxypropyl methylcellulose stearoxy ether, hydroxypropyl starch, hydroxypropyl starch phosphate, hydroxystearyl cetyl ether, isobutyl methyl tetrahydropyranol, isoeugenol, isolongifolene epoxide, isopropyl hydroxycetyl ether, isostearamidopropyl epoxypropyl dimonium chloride, isostearyl glucoside, isostearyl glyceryl ether, isostearyl glyceryl pentaerythrityl ether, lactobionic acid, laureth-5 butyl ether, lauryl polyglyceryl-6 cetearyl glycol ether, melatonin, menthone glycerin acetal, 3-methoxybutanol, methoxydiglycol, methoxyethanol, methoxyethanol acetate, methoxyindane, methoxyisopropanol, methoxyisopropyl acetate, methoxymethylbutanol, methoxy PEG-7 ascorbic acid, methoxypropylgluconamide, methoxytrimethylphenyl dihydroxyphenyl propanol, methylal, methyl ethylcellulose, methyl eugenol, methyl hexyl ether, methylsilanol ascorbate, myristyl-PG hydroxyethyl decanamide, neohesperidin dihydrochalcone, 4-nitroguaiacol, nonoxynyl hydroxyethylcellulose, oleyl glyceryl ether, palmitoyl methoxytryptamine, panthenyl ethyl ether, panthenyl ethyl ether acetate, panthenyl hydroxypropyl steardimonium chloride, PEG-3 2,2'-di-p-phenylenediamine, PEG-4 ditallow ether, PEG-9 methyl ether dimethicone, PEG-150 pentaerythrityl tetrastearate, perfluorohexylethyl dimethylbutyl ether, perfluorononyl octyldodecyl glycol meadowfoamate, permethrin, p-phenetidine, phenoxyethanol, phenoxyethylparaben, phenoxyisopropanol, piperonyl butoxide, polyglyceryl-3 cetyl ether, polyglyceryl-3 decyltetradecyl ether, polyglyceryl-3 hydroxylauryl ether, polyglyceryl-2 lanolin alcohol ether, polyglyceryl-4 lauryl ether, polyglyceryl-2 oleyl ether, polyglyceryl-4 oleyl ether, polyglyceryl sorbitol, polyvinyl methyl ether, polyvinyl stearyl ether, potassium lauryl hydroxypropyl sulfonate, potassium methoxycinnamate, acetyl glucosamine, aminopropyl ascorbyl phosphate, ascorbic acid, ascorbyl dipalmitate, ascorbyl methylsilanol pectinate, ascorbyl palmitate, ascorbyl stearate, bis-hydroxyethyl tromethamine, calcium fructoheptonate, calcium glucoheptonate, calcium glycerophosphate, dithiaoctanediol, erythritol, ethanolamine glycerophosphate, ferrous glucoheptonate, fructose, galactaric acid, galacturonic acid, glucamine, glucoheptonolactone, gluconic acid, gluconolactone, glucosamine, glucose, glucose glutamate, glucosylrutin, glucuronic acid, hesperidin methyl chalcone, hydroxyethyl sorbitol, hydroxystearyl methylglucamine, inositol, isostearyl glyceryl pentaerythrityl ether, lactitol, lactose, laurimino bispropanediol, lauroyl methyl glucamide, lauryl methyl gluceth-10 hydroxypropyldimonium chloride, lithium gluconate, magnesium glucoheptonate, maltitol, maltitol laurate, maltose, mannan, mannitan laurate, mannitan oleate, mannitol, mannose, methoxy PEG-7 ascorbic acid, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, methylglucamine, methylpropanediol, methylsilanol ascorbate, nickel gluconate, phytantriol, polyglucuronic acid, potassium glucoheptonate, potato starch modified, PPG1-PEG-9 lauryl glycol ether, PPG-9 diglyceryl ether, propylene glycol butyl ether, propylene glycol myristyl ether, propylene glycol propyl ether, quassin, quercetin, riboflavin, ribonic acid, rutin, sclareolide, silanetriol trehalose ether, sodium butoxyethoxy acetate, sodium glucuronate, sodium hexyldiphenyl ether sulfonate, sodium hydroxypropyl starch phosphate, sodium lauryl glycol carboxylate, sodium PEG-8 palm glycerides carboxylate, sodium riboflavin phosphate, sorbeth-20, sorbeth-30, sorbeth-40, sorbeth-6, sorbityl acetate, sorbityl furfural, sorbityl silanediol, stearylvinyl ether-MA copolymer, sucrose, TEA-lauryl ether, tetrahydrodemethoxydiferuloylmethane, tetrahydrodiferuloylmethane, thiodiglycol, thioglycerin, tolnaftate, triethoxycaprylylsilane, triethylene glycol, trihydroxypalmitamidohydroxypropyl myristyl ether, trimethoxycaprylylsilane, trimethyl pentanol hydroxyethyl ether, tripropylene glycol, tris(hydroxymethyl) nitromethane, tris-ethoxydiglycol phosphate, tromethamine, troxerutin, ubiquinone, vanillyl butyl ether, xylitol, xylose, zinc glucoheptonate, 1,2 hexanediol, glycerine, butyl glycerol ether, hexylene glycol, sorbitol, isopropyl glycerol ether, and combinations of two or more of the above described ingredients.

Component (i) is preferably selected from the group consisting of diethylene glycol, triethylene glycol, dipropylene glycol, 1,2-propylene glycol, 1,3-propylene glycol, 2-methyl-1,3-propanediol, 1,4-butylene glycol, 1,2-butylene glycol, 1,3-butylene glycol, 2,3-butylene glycol or combinations thereof. It is especially preferred that the non-aqueous polar solvent, Component (i), is selected from the group consisting of 1,2-propylene glycol (commonly referred to as propylene glycol), dipropylene glycol, 2-methyl-1,3-propanediol, 1,3-butylene glycol, and combinations thereof, with propylene glycol being most preferred.

Component (i), the non-aqueous polar solvent, is present in the microemulsions of this invention in an amount from 10 to 50 weight parts, and preferably from 20 to 40 weight parts, said weight parts being based on the total weight of the composition.

The non-polar solvent, Component (ii) must be immiscible with Component (i). Component (ii) comprises a hydrocarbon fluid, a silicone solvent, or a combination thereof. The hydrocarbon fluids are exemplified by organic hydrocarbon fluids such as halogenated hydrocarbon fluids, aliphatic hydrocarbon fluids, aromatic hydrocarbon fluids, and mixtures of aromatic and aliphatic hydrocarbon fluids. The hydrocarbon fluids usually contain about 6 to about 12 carbon atoms. Examples of suitable hydrocarbon fluids include perchloroethylene, benzene, xylene, toluene, mineral oil fractions, kerosenes, naphthas, and petroleum fractions. Particularly preferred are isoparaffinic hydrocarbon fluids exemplified by isoparaffin fluids available from ExxonMobil Chemical Company, Houston, Tex. U.S.A, sold as Isopar® M Fluid (a C13–C14 Isoparaffin), Isopar® C Fluid (a C7–C8 Isoparaffin), Isopar® E Fluid (a C8–C9 Isoparaffin), Isopar® G Fluid (a C10–11 Isoparaffin), Isopar® L Fluid (a C11–C13 Isoparaffin), Isopar® H Fluid (a C11–C12 Isoparaffin), and combinations thereof.

The silicone solvent can be a cyclosiloxane exemplified by octamethylcyclotetrasiloxane, decamethylcyclopentasiloxane, and dodecamethylcyclohexasiloxane, or combinations thereof, with decamethylcyclopentasiloxane being preferred. The silicone solvent can also be a trimethylsiloxy-endblocked polydimethylsiloxane having a viscosity of from 0.65 to 5 mm$^2$/s (1 mm$^2$/s=1 centistoke). The silicone solvent can also be a combination of the above-described cyclosiloxane and the above-described trimethylsiloxy-endblocked polydimethylsiloxane.

Component (ii), the non-polar solvent, is present in the microemulsions of this invention in an amount from 10 to 89 weight parts, and preferably from 40 to 60 weight parts, said weight parts being based on the total weight of the composition.

Component (iii) is at least one oxyalkylene-containing polydiorganosiloxane having its formula selected from the group consisting of $R_3SiO(RR^1SiO)_ySiR_3$,
$R_3SiO(R_2SiO)_x(RR^1SiO)_ySiR_3$,
$R^1R_2SiO(RR^1SiO)_zSiR_2R^1$,
$R^1R_2SiO(R_2SiO)_xSiR_2R^1$,
$R^1R_2SiO(R_2SiO)_x(RR^1SiO)_zSiR_2R^1$, and a cyclosiloxane copolymer having the formula —(Me$_2$SiO)$_m$(MeR$^1$SiO)$_n$—wherein R denotes an alkyl group containing from 1 to 6 carbon atoms, R$^1$denotes a group having its formula selected from the group consisting of —(CH$_2$)$_a$(OCH$_2$CH$_2$)$_b$OR$^2$,
—(CH$_2$)$_a$(OCH$_2$CH(CH$_3$))$_c$OR$^2$,
—(CH$_2$)$_a$(OCH$_2$CH(CH$_2$CH$_3$))$_d$OR$^2$,
—(CH$_2$)$_a$(OCH$_2$CH$_2$)$_b$(OCH$_2$CH(CH$_3$))$_c$OR$^2$,
—(CH$_2$)$_a$(OCH$_2$CH$_2$)$_b$(OCH$_2$CH(CH$_2$CH$_3$))$_d$OR$^2$, and
—(CH$_2$)$_a$(OCH$_2$CH$_2$)$_b$(OCH$_2$CH(CH$_3$))$_c$(OCH$_2$CH(CH$_2$CH$_3$))$_d$OR$^2$ wherein a has a value of 3 to 11, b has a value of 1 to 20, c has a value of 1 to 10, d has a value of 1 to 4, and R$^2$ is selected from the group consisting of hydrogen, an alkyl group, and an acyl group, x has a value of 1 to 400, y has a value of 1 to 40, z has a value of 1 to 40, m has a value of 1 to 6, n has a value of 1 to 6, and the value of m+n is from 3 to 6.

For purposes of this invention the various siloxane units and the oxyethylene, oxypropylene, and oxybutylene units may be distributed randomly throughout their respective chains or in respective blocks of such units or in a combination of random or block distributions.

The alkyl groups of R are exemplified by methyl, ethyl, propyl, butyl, pentyl, and hexyl. Preferably R is methyl. The alkyl groups of R$^2$ are as described above for R, with methyl being preferred. It is preferred that R$^2$ is hydrogen or methyl, with hydrogen being especially preferred. The acyl groups are exemplified by —C(O)CH$_3$. Preferably x has a value of 10 to 200, y has a value of 1 to 20, and z has a value of 1 to 20. It is also preferred that m has a value of 3 to 5 and n has a value of 1 to 2, with the value of m+n being from 3 to 6.

It is especially preferred that R$^1$is a group having the formula —(CH$_2$)$_a$(OCH$_2$CH$_2$)$_b$OR$^2$ wherein a has a value of 3, b has a value of 5 to 15 and R$^2$ is hydrogen.

Component (iii), the oxyalkylene-containing polydiorganosiloxane, is present in the microemulsions of this invention in an amount from 1 to 40 weight parts, and preferably from 10 to 20 weight parts, said weight parts being based on the total weight of the composition.

The microemulsions of this invention may also further comprise (iv) an additional solvent exemplified by polyhydric alcohols such as glycerol, monohydric alcohols such as ethanol, fatty alcohols such as isostearyl alcohol, and alkoxylated ethers such as 2-butoxyethanol (ethylene glycol monobutyl ether) which is commercially available as butyl cellosolve from Union Carbide. The additional solvent can comprise up to 20 weight parts per 100 weight parts of microemulsion, and preferably comprises 1 to 10 weight parts per 100 weight parts of microemulsion.

The microemulsions of this invention can further comprise (v) a personal care active ingredient exemplified by antiperspirants salts, moisturizers, occlusive agents, sunscreens, anti-microbial agents, drugs, vitamins such as Vitamin E, emollients, humectants, colorants, and perfumes. The antiperspirant salts are typically water-soluble inorganic astringent antiperspiration agents which are preferably salts of aluminum, zirconium or zinc. Examples of these suitable antihydrotic agents are aluminum chloride, aluminum chlorohydrate, aluminum dichlorohydrate, aluminum sesquichlorohydrate and complex compounds thereof with 1,2-propylene glycol, aluminum hydroxyallantoinate, aluminum chloride tartrate, aluminum/zirconium trichlorohydrate, aluminum/zirconium tetrachlorohydrate, aluminum/zirconium pentachlorohydrate and complex compounds thereof with amino acids, for example with glycine. However, aluminum hydroxychlorides and adducts thereof with water-soluble glycols are particularly suitable. Water-soluble salts are understood to be salts of which at least 1% by weight dissolve in water at 20° C. The personal care active ingredient described above can be added to the microemulsion at any time during or after formation of the microemulsion, however it is preferred that the personal care active ingredient is added to the polar solvent or the non-polar solvent prior to formation of the microemulsion. The personal care active ingredient can be added in any amount to the microemulsion sufficient to impart the personal care benefits desired in the microemulsion, it is preferred however that from about 1 to 50 weight parts be added, and preferably from 1 to 25 weight parts be added, per 100 weight parts of microemulsion.

In a second embodiment, this invention relates to a method of making an optically clear one-phase microemulsion which is transparent at temperature of from 0–70° C. comprising (I) mixing (i) at least one non-aqueous polar solvent, (ii) at least one non-polar solvent immiscible with (i), and (iii) at least one oxyalkylene-containing polydiorganosiloxane having its formula selected from the group consisting of $R_3SiO(RR^1SiO)_ySiR_3$,
$R_3SiO(R_2SiO)_x(RR^1SiO)_ySiR_3$,
$R^1R_2SiO(RR^1SiO)_zSiR_2R^1$,
$R^1R_2SiO(R_2SiO)_xSiR_2R^1$,
$R^1R_2SiO(R_2SiO)_x(RR^1SiO)_zSiR_2R^1$, and a cyclosiloxane copolymer having the formula —$(Me_2SiO)_m(MeR^1SiO)_n$—wherein R denotes an alkyl group containing from 1 to 6 carbon atoms, $R^1$ denotes a group having its formula selected from the group consisting of —$(CH_2)_a(OCH_2CH_2)_bOR^2$,
—$(CH_2)_a(OCH_2CH(CH_3))_cOR^2$,
—$(CH_2)_a(OCH_2CH(CH_2CH_3))_dOR^2$,
—$(CH_2)_a(OCH_2CH_2)_b(OCH_2CH(CH_3))_cOR^2$,
—$(CH_2)_a(OCH_2CH_2)_b(OCH_2CH(CH_2CH_3))_dOR^2$, and
—$(CH_2)_a(OCH_2CH_2)_b(OCH_2CH(CH_3))_c(OCH_2CH(CH_2CH_3))_dOR^2$ wherein a has a value of 3 to 11, b has a value of 1 to 20, c has a value of 1 to 10, d has a value of 1 to 4, and $R^2$ is selected from the group consisting of hydrogen, an alkyl group, and an acyl group, x has a value of 1 to 400, y has a value of 1 to 40, z has a value of 1 to 40, m has a value of 1 to 6, and n has a value of 1 to 6. Components (i), (ii), and (iii) are as described above including preferred embodiments and amounts thereof.

The method of this invention can further comprise adding an additional solvent during or after Step (I). The additional solvent is as described above including preferred embodiments and amounts thereof.

The method of this invention can further comprise adding a personal care active ingredient during or after Step (I). The personal care active ingredient is as described above including preferred embodiments and amounts thereof.

The microemulsions of this invention may be prepared by mixing (or mechanically agitating) components (i)-(iii), and any optional components, to form a homogenous mixture. This may be accomplished by any convenient mixing method known in the art exemplified by a spatula, mechanical stirrers, in-line mixing systems containing baffles and/or blades, powered in-line mixers, homogenizers, a drum roller, a three-roll mill, a sigma blade mixer, a bread dough mixer, and a two roll mill. The order of mixing is not considered critical.

EXAMPLES

Example 1

An optically clear one-phase microemulsion that remained transparent throughout temperature range of from 0 to 70° C. was prepared by adding to a container and mixing 35 weight parts of decamethylcyclopentasiloxane and 30 weight parts of an oxyalkylene-containing polydiorganosiloxane having the formula $Me_3SiO(Me_2SiO)_{22}(MeRSiO)_{22}SiMe_3$ where R is a group having the formula —$(CH_2)_3(OCH_2CH_2)_{12}OH$ (hereinafter denoted OXYALKYLENE-CONTAINING POLYDIORGANOSILOXANE 1). Subsequently, 35 weight parts of propylene glycol were added to the container, and the mixture was mixed for about 3 minutes using a Hauschild Speedmixer.

Example 2

An optically clear one-phase microemulsion that remained transparent throughout temperature range of from 0 to 70° C. was prepared by adding to a container and mixing 30 weight parts of decamethylcyclopentasiloxane and 40 weight parts of OXYALKYLENE-CONTAINING POLYDIORGANOSILOXANE 1. Subsequently, 27 weight parts of propylene glycol and 3 weight parts of glycerol were added to the container, and the mixture was mixed for about three minutes using a Hauschild Speedmixer.

Example 3

An optically clear one-phase microemulsion that remained transparent throughout temperature range of from 0 to 70° C. was prepared by adding to a container and mixing 35 weight parts of decamethylcyclopentasiloxane and 30 weight parts of OXYALKYLENE-CONTAINING POLYDIORGANOSILOXANE 1. Subsequently, 33.25 weight parts of propylene glycol and 1.75 weight parts of isostearyl alcohol were added to the container, and the mixture was mixed for three minutes using a Hauschild Speedmixer.

Example 4

An optically clear one-phase microemulsion that remained transparent throughout temperature range of from 0 to 70° C. was prepared by adding to a container and mixing 35 weight parts of decamethylcyclopentasiloxane and 30 weight parts of OXYALKYLENE-CONTAINING POLYDIORGANOSILOXANE 1. Subsequently, 31.5 weight parts of propylene glycol and 3.5 weight parts of ethanol were added to the container, and the mixture was mixed for three minutes using a Hauschild Speedmixer.

Example 5

An optically clear one-phase microemulsion that remained transparent throughout temperature range of from 0 to 70° C. was prepared by adding to a container and mixing 35 weight parts of trimethylsiloxy-endblocked polydimethylsiloxane having a viscosity of 2 mm²/s and 30 weight parts of OXYALKYLENE-CONTAINING POLYDIORGANOSILOXANE 1. Subsequently, 35 weight parts of propylene glycol were added to the container, and the mixture was mixed for three minutes using a Hauschild Speedmixer.

Example 6

An optically clear one-phase microemulsion that remained transparent throughout temperature range of from 0 to 70° C. was prepared by adding to a container and mixing 20 weight parts of decamethylcyclopentasiloxane and 60 weight parts of an oxyalkylene-containing polydiorganosiloxane having the formula $R^1Me_2SiO(Me_2SiO)_{15}SiMe_2R^1$ where $R^1$ is a group having the formula —$(CH_2)_3(OCH_2CH_2)_{12}OH$ (hereinafter denoted OXYALKYLENE-CONTAINING POLYDIORGANOSILOXANE 2). Subsequently, 20 weight parts of propylene glycol were added to the container, and the mixture was mixed for three minutes using a Hauschild Speedmixer.

Example 7

An optically clear one-phase microemulsion that remained transparent throughout temperature range of from 0 to 70° C. was prepared by adding to a container and mixing 20 weight parts of decamethylcyclopentasiloxane and 40 weight parts of OXYALKYLENE-CONTAINING POLYDIORGANOSILOXANE 2. Subsequently, 18 weight parts of propylene glycol and 2 weight parts of glycerol were added to the container, and the mixture was mixed for three minutes using a Hauschild Speedmixer.

Example 8

An optically clear one-phase microemulsion that remained transparent throughout temperature range of from 0 to 70° C. was prepared by adding to a container and mixing 20 weight parts of decamethylcyclopentasiloxane and 40 weight parts of OXYALKYLENE-CONTAINING POLYDIORGANOSILOXANE 2. Subsequently, 18 weight parts of propylene glycol and 2 weight parts of ethanol were added to the container, and the mixture was mixed for three minutes using a Hauschild Speedmixer.

Example 9

An optically clear one-phase microemulsion that remained transparent throughout temperature range of from 0 to 70° C. was prepared by adding to a container and mixing 20 weight parts of decamethylcyclopentasiloxane and 40 weight parts of an oxyalkylene-containing polydiorganosiloxane having the formula $Me_3SiO(MeRSiO)SiMe_3$ where R is a group having the formula —$(CH_2)_3(OCH_2CH_2)_7OH$ (hereinafter denoted OXYALKYLENE-CONTAINING POLYDIORGANOSILOXANE 3). Subsequently, 20 weight parts of propylene glycol were added to the container, and the mixture was mixed for three minutes using a Hauschild Speedmixer.

Example 10

An optically clear one-phase microemulsion that remained transparent throughout temperature range of from 0 to 70° C. was prepared by adding to a container and mixing 20 weight parts of decamethylcyclopentasiloxane and 40 weight parts of OXYALKYLENE-CONTAINING POLYDIORGANOSILOXANE 3. Subsequently, 18 weight parts of propylene glycol and 2 weight parts of glycerol were added to the container, and the mixture was mixed for three minutes using a Hauschild Speedmixer.

Example 11

An optically clear one-phase microemulsion that remained transparent throughout temperature range of from 0 to 70° C. was prepared by adding to a container and mixing 21 weight parts of decamethylcyclopentasiloxane and 58 weight parts of an oxyalkylene-containing polydiorganosiloxane having the formula $Me_3SiO(Me_2SiO)_{8.5}(MeRSiO)_{3.5}SiMe_3$ where R is a group having the formula —$(CH_2)_3(OCH_2CH_2)_7OH$ (hereinafter denoted OXYALKYLENE-CONTAINING POLYDIORGANOSILOXANE 4). Subsequently, 19 weight parts of propylene glycol and 2 weight parts of glycerol were added to the container, and the mixture was mixed for three minutes using a Hauschild Speedmixer.

Example 12

An optically clear one-phase microemulsion that remained transparent throughout temperature range of from 0 to 70° C. was prepared by adding to a container and mixing 30 weight parts of Isopar® G and 40 weight parts of OXYALKYLENE-CONTAINING POLYDIORGANOSILOXANE 1. Subsequently, 30 weight parts of propylene glycol were added to the container, and the mixture was mixed for three minutes using a Hauschild Speedmixer.

Example 13

An optically clear one-phase microemulsion that remained transparent throughout temperature range of from 0 to 70° C. was prepared by adding to a container and mixing 25 weight parts of decamethylcyclopentasiloxane containing octylmethoxycinnamate and 50 weight parts of OXYALKYLENE-CONTAINING POLYDIORGANOSILOXANE 1. Subsequently, 25 weight parts of propylene glycol solution were added to the container, and the mixture was mixed for three minutes using a Hauschild Speedmixer.

Example 14

An optically clear one-phase microemulsion that remained transparent throughout temperature range of from 0 to 70° C. was prepared by adding to a container and mixing 32.5 weight parts of decamethylcyclopentasiloxane, 1.625 weight parts of Vitamin E and 35 weight parts of OXYALKYLENE-CONTAINING POLYDIORGANOSILOXANE 1. Subsequently, 30.875 weight parts of propylene glycol solution were added to the container, and the mixture was mixed for three minutes using a Hauschild Speedmixer.

Example 15

An optically clear one-phase microemulsion that remained transparent throughout temperature range of from 0 to 70° C. was prepared by adding to a container and mixing 30 weight parts of decamethylcyclopentasiloxane and 40 weight parts of an oxyalkylene-containing polydiorganosiloxane having the formula $Me_3SiO(MeRSiO)_{164}SiMe_3$ where R is a group having the formula —$(CH_2)_3(OCH_2CH_2)_7OH$ (hereinafter denoted OXYALKYLENE-CONTAINING POLYDIORGANOSILOXANE 5). Subsequently, 30 weight parts of a 30% by weight aluminum zirconium tetrachlorohydrex/glycine in propylene glycol solution were added to the container, and the mixture was mixed for three minutes using a Hauschild Speedmixer.

That which is claimed is:

1. An optically clear one-phase microemulsion which is transparent throughout temperature range of from 0 to 70° C. comprising:

(i) at least one non-aqueous polar solvent;

(ii) at least one non-polar solvent immiscible with (i); and (iii) at least one oxyalkylene-containing polydiorganosiloxane having its formula selected from the group consisting of
$R_3SiO(RR^1SiO)_ySiR_3$,
$R_3SiO(R_2SiO)_x(RR^1SiO)_ySiR_3$,
$R^1R_2SiO(RR^1SiO)_zSiR_2R^1$,
$R^1R_2SiO(R_2SiO)_xSiR_2R^1$,
$R^1R_2SiO(R_2SiO)_x(RR^1SiO)_zSiR_2R^1$, and
a cyclosiloxane copolymer having the formula —$(Me_2SiO)_m(MeR^1SiO)_n$—
wherein R denotes an alkyl group containing from 1 to 6 carbon atoms, $R^1$ denotes a group having its formula selected from the group consisting of
—$(CH_2)_a(OCH_2CH_2)_bOR^2$,
—$(CH_2)_a(OCH_2CH(CH_3))_cOR^2$,
—$(CH_2)_a(OCH_2CH(CH_2CH_3))_dOR^2$,
—$(CH_2)_a(OCH_2CH_2)_b(OCH_2CH(CH_3))_cOR^2$,
—$(CH_2)_a(OCH_2CH_2)_b(OCH_2CH(CH_2CH_3))_dOR^2$, and
—$(CH_2)_a(OCH_2CH_2)_b(OCH_2CH(CH_3))_c(OCH_2CH(CH_2CH_3))_dOR^2$
wherein a has a value of 3 to 11, b has a value of 1 to 20, c has a value of 1 to 10, d has a value of 1 to 4, and $R^2$ is selected from the group consisting of hydrogen, an alkyl group, and an acyl group, x has a value of 1 to 400, y has a value of 1 to 40, z has a value of 1 to 40, m has a value of 1 to 6, n has a value of 1 to 6, and the value of m+n is from 3 to 6.

2. A microemulsion according to claim 1, wherein (i) is selected from the group consisting of diethylene glycol, triethylene glycol, dipropylene glycol, 1,2-propylene glycol, 1,3-propylene glycol, 2-methyl-1,3-propanediol, 1,4-butylene glycol, 1,2-butylene glycol, 1,3-butylene glycol, 2,3-butylene glycol, 1,2-hexanediol, glycerine, butyl glycerol ether, hexylene glycol, sorbitol, isopropyl glycerol ether, and combinations thereof.

3. A microemulsion according to claim 1, wherein (i) is selected from the group consisting of 1,2-propylene glycol, dipropylene glycol, 2-methyl-1,3-propanediol, 1,3-butylene glycol, and combinations thereof.

4. A microemulsion according to claim 1, wherein (ii) is a hydrocarbon fluid, a silicone solvent, or a combination thereof.

5. A microemulsion according to claim 2, wherein (ii) is a hydrocarbon fluid, a silicone solvent, or a combination thereof.

6. A microemulsion according to claim 3, wherein (ii) is a hydrocarbon fluid, a silicone solvent, or a combination thereof.

7. A microemulsion according to claim 4, wherein the hydrocarbon fluid is an isoparaffinic hydrocarbon fluid, and the silicone solvent is selected from the group consisting of octamethylcyclotetrasiloxane, decamethylcyclopentasiloxane, dodecamethylcyclohexasiloxane, trimethylsiloxy-endblocked polydimethylsiloxanes having a viscosity of from 0.65 to 5 mm²/s, and combinations thereof.

8. A microemulsion according to claim 5, wherein the hydrocarbon is an isoparaffinic hydrocarbon fluid, and the silicone solvent is selected from the group consisting of octamethylcyclotetrasiloxane, decamethylcyclopentasiloxane, dodecamethylcyclohexasiloxane, trimethylsiloxy-endblocked polydimethylsiloxanes having a viscosity of from 0.65 to 5 mm₂/s, and combinations thereof.

9. A microemulsion according to claim 6, wherein the hydrocarbon is an isoparaffinic hydrocarbon fluid, and the silicone solvent is selected from the group consisting of octamethylcyclotetrasiloxane, decamethylcyclopentasiloxane, dodecamethylcyclohexasiloxane, trimethylsiloxy-endblocked polydimethylsiloxanes having a viscosity of from 0.65 to 5 mm²/s, and combinations thereof.

10. A microemulsion according to claim 1, wherein R is methyl, $R^2$ is hydrogen, x has a value of 10 to 200, y has a value of 1 to 20, z has a value of 1 to 20, m has a value of 3 to 5, n has a value of 1 to 2, and the value of m+n is 3 to 6.

11. A microemulsion according to claim 7, wherein R is methyl, $R^2$ is hydrogen, x has a value of 10 to 200, y has a value of 1 to 20, z has a value of 1 to 20, m has a value of 3 to 5, n has a value of 1 to 2, and the value of m+n is 3 to 6.

12. A microemulsion according to claim 8, wherein R is methyl, $R^2$ is hydrogen, x has a value of 10 to 200, y has a value of 1 to 20, z has a value of 1 to 20, m has a value of 3 to 5, n has a value of 1 to 2, and the value of m+n is 3 to 6.

13. A microemulsion according to claim 9, wherein R is methyl, $R^2$ is hydrogen, x has a value of 10 to 200, y has a value of 1 to 20, z has a value of 1 to 20, m has a value of 3 to 5, n has a value of 1 to 2, and the value of m+n is 3 to 6.

14. A microemulsion according to claim 1, wherein (i) is 1,2-propylene glycol, (ii) is selected from the group consisting of isoparaffinic hydrocarbon fluids, decamethylcyclopentasiloxane, trimethylsiloxy-endblocked polydimethylsiloxanes having a viscosity of from 0.65 to 5 mm²/s, and combinations thereof, and wherein R is methyl, $R^1$ is a group having the formula —$(CH_2)_a(OCH_2CH_2)_bOH$ wherein a has a value of 3, b has a value of 5 to 15, x has a value of 10 to 200, y has a value of 1 to 20, z has a value of 1 to 20, m has a value of 3 to 5, n has a value of 1 to 2, and the value of m+n is 3 to 6.

15. A microemulsion according to claim 1, wherein the microemulsion further comprises (iv) a solvent selected from the group consisting of polyhydric alcohols, monohydric alcohols, fatty alcohols, and alkoxylated ethers.

16. A microemulsion according to claim 15, wherein (iv) is selected from the group consisting of glycerol, ethanol, isostearyl alcohol, and ethylene glycol monobutyl ether.

17. A microemulsion according to claim 11, wherein the microemulsion further comprises (iv) a solvent selected from the group consisting of glycerol, ethanol, isostearyl alcohol, and ethylene glycol monobutyl ether.

18. A microemulsion according to claim 12, wherein the microemulsion further comprises (iv) a solvent selected from the group consisting of glycerol, ethanol, isostearyl alcohol, and ethylene glycol monobutyl ether.

19. A microemulsion according to claim 13, wherein the microemulsion further comprises (iv) a solvent selected from the group consisting of glycerol, ethanol, isostearyl alcohol, and ethylene glycol monobutyl ether.

20. A microemulsion according to claim 14, wherein the microemulsion further comprises (iv) a solvent selected from the group consisting of glycerol, ethanol, isostearyl alcohol, and ethylene glycol monobutyl ether.

21. A microemulsion according to claim 1, wherein the microemulsion further comprises (v) a personal care active ingredient.

22. A microemulsion according to claim 11, wherein the microemulsion further comprises (v) a personal care active ingredient.

23. A microemulsion according to claim 12, wherein the microemulsion further comprises (v) a personal care active ingredient.

24. A microemulsion according to claim 13, wherein the microemulsion further comprises (v) a personal care active ingredient.

25. A microemulsion according to claim 14, wherein the microemulsion further comprises (v) a personal care active ingredient.

26. A microemulsion according to claim 15, wherein the microemulsion further comprises (v) a personal care active ingredient.

27. A microemulsion according to claim 16, wherein the microemulsion further comprises (v) a personal care active ingredient.

28. A method of making an optically clear one-phase microemulsion which is transparent throughout a temperature range of from 0 to 70° C. comprising:
   (I) mixing
      (i) at least one non-aqueous polar solvent;
      (ii) at least one non-polar solvent immiscible with (i); and
      (iii) at least one oxyalkylene-containing polydiorganosiloxane having its formula selected from the group consisting of
         $R_3SiO(RR^1SiO)_ySiR_3$,
         $R_3SiO(R_2SiO)_x(RR^1SiO)_ySiR_3$,
         $R^1R_2SiO(RR^1SiO)_zSiR_2R^1$,
         $R^1R_2SiO(R_2SiO)_xSiR_2R^1$,
         $R^1R_2SiO(R_2SiO)_x(RR^1SiO)_zSiR_2R^1$,
         and a cyclosiloxane copolymer having the formula
         $—(Me_2SiO)_m(MeR^1SiO)_n—$ wherein R denotes an alkyl group containing from 1 to 6 carbon atoms, $R^1$ denotes a group having its formula selected from the group consisting of
   $—(CH_2)_a(OCH_2CH_2)_bOR^2$
   $—(CH_2)_a(OCH_2CH(CH_3))_cOR^2$
   $—(CH_2)_a(OCH_2CH(CH_2CH_3))_dOR^2$
   $—(CH_2)_a(OCH_2CH_2)_b(OCH_2CH(CH_3))_cOR^2$
   $—(CH_2)_a(OCH_2CH_2)_b(OCH_2CH(CH_2CH_3))_dOR_2$
   $—(CH_2)_a(OCH_2CH_2)_b(OCH_2CH(CH_3))_c(OCH_2CH(CH_2CH_3))_dOR_2$ wherein a has a value of 3 to 11, b has a value of 1 to 20, c has a value of 1 to 10, d has a value of 1 to 4, and $R^2$ is selected from the group consisting of hydrogen, an alkyl group, and an acyl group, x has a value of 1 to 400, y has a value of 1 to 40, z has a value of 1 to 40, m has a value of 1 to 6, n has a value of 1 to 6, and the value of m+n is from 3 to 6.

29. A method according to claim 28, wherein the method further comprises adding a solvent selected from the group consisting of polyhydric alcohols, monohydric alcohols, fatty alcohols, and alkoxylated ethers during or after Step (I).

30. A method according to claim 28, wherein the method further comprises adding a personal care active ingredient during or after Step (I).

31. A method according to claim 29, wherein the method further comprises adding a personal care active ingredient during or after Step (I).

* * * * *